United States Patent
von Gutfeld et al.

(10) Patent No.: US 6,245,005 B1
(45) Date of Patent: Jun. 12, 2001

(54) METHOD AND APPARATUS FOR FACILITATING RADIATION TREATMENT OF DEEP TUMORS

(75) Inventors: Robert Jacob von Gutfeld, New York; James Francis Ziegler, Yorktown Heights, both of NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/356,179

(22) Filed: Jul. 16, 1999

(51) Int. Cl.[7] .................................................. A16N 5/00
(52) U.S. Cl. .............................................................. 600/1
(58) Field of Search .................... 600/411, 1, 2, 600/3, 4, 5, 6, 7; 250/370

(56) References Cited

U.S. PATENT DOCUMENTS 4,572,954 * 2/1986 Josephson et al. .................. 250/370
5,704,890 * 1/1998 Bliss et al. ............................. 600/1

* cited by examiner

Primary Examiner—Cary O'Connor
Assistant Examiner—Brian Szmal
(74) Attorney, Agent, or Firm—Ohlandt, Greeley, Ruggiero & Perle, LLP; Casey P. August, Esq.

(57) ABSTRACT

The invention allows more accurate localization of radiation volumes during radiation treatment of tumors. The equipment includes radiation detector elements placed behind the patient during radiation, for treatment of a tumor condition. Such a detector may be constructed of semiconductor or a scintillating material. The radiation treatment plan for the patient includes an additional calculation of the treatment beam energy required for to enable the treatment beam to transit the patient. The energy required for patient transit is then measured, using a treatment beam with a beam current below that which will induce significant tissue damage. The experimental transit flux is then compared to the calculated transit flux, and the difference is used to correct the beam transport parameters in the original radiation treatment plan. Hence lower radiation doses and smaller radiation volumes can be achieved, reducing deleterious radiation side effects.

19 Claims, 6 Drawing Sheets

METHOD AND APPARATUS FOR FACILITATING RADIATION TREATMENT OF DEEP TUMORS

FIELD OF THE INVENTION

The invention relates to a method and apparatus for enabling increased accuracy of localization of radiation volumes and beam treatment energies during radiation treatment of tumors.

BACKGROUND OF THE INVENTION

Medical radiation treatments of deep tumors are planned based on CAT (computer aided tomography) or MRI (magnetic resonance imaging) cross-sectional views. Such views identify and locate a treatment volume relative to other major organs. A major problem occurs in translating these views to radiation treatment parameters, especially the energy of the treatment-beam particles. For example, a CAT scan reconstructs internal features by measuring the absorption of X-rays by the body from various angles. The X-rays used are of such high energy that greater than 90% are transmitted through the body without absorption.

However, radiation treatment requires that the irradiating beam stop at the bottom of the volume of the treatment region, to prevent damage to deeper organs. If particles are used for the radiation treatment (such as protons or electrons), a large correction must be applied to relate the energy loss of the particles to the X-ray absorption values of the CAT scan. Similar considerations apply to MRI scans that are converted to radiation treatment parameters.

In summary, the diagnostic phase is implemented through use of CAT or MRI scans, however the treatment phase may be done either with a radiation beam of different energy or with different types of particle beams. Stepping from the diagnostic to the treatment phase requires theoretical assumptions about how the body interacts to the various types of radiation. As an example, consider the treatment of a prostate cancer located by CAT scans. The radiation volume is identified by use of CAT images. The radiation treatment chosen involves the use of a proton beam that penetrates approximately 12 cm to the prostate tumor.

The treatment planner needs to convert the CAT images to equivalent proton energy loss, so that the initial proton energy will allow the protons to penetrate to the prostate and no further. This is done using a conversion table for deriving Hounsfield Units (HU), which relate the CAT image density to body density. From this the planner can model the treatment phase, using values of the proton energy loss.

It is important that the incident protons not penetrate further than the prostate gland, for the colon (just distal to the prostate) is much more sensitive to radiation and may be harmed by small amounts of proton irradiation. It has recently been shown that the required conversion factor, HU, from CAT scans to proton energy loss, may be inaccurate for various organs and tissue types. This is reported in "Range Precision of Therapeutic Proton Beams", B. Schaffner, Ph.D. Thesis, submitted to the Swiss Federal Institute of Technology, Zurich (Switzerland), 1997.

Further, CAT scans are rarely taken with the patient on the treatment gurney. For deep tumors, there may be significant organ motion between the time of a CAT scan and the radiation treatment, limiting the CAT scan reliability for predicting body density encountered by the treatment beam. For example, the CAT scan may show 6 cm of partially-full small intestines that the proton beam must penetrate to reach the prostate. But at the time of irradiation treatment (perhaps several days later), there may be only 5 cm of empty intestines to be penetrated. This kind of "motion" error and also errors in the HU units, may be compensated for by increasing the volume of irradiation, leading to peripheral organ damage and increased radiation burden to the patient.

Accordingly, it is an object of the invention to provide a method and apparatus for adjusting a treatment beam so as to assure a desired level of beam energy in a treatment volume.

It is a further object of the invention to provide a method and apparatus for adjusting the positioning of a treatment beam so as to assure a desired beam orientation with respect to a treatment volume.

SUMMARY OF THE INVENTION

This invention enables in-situ correction of patient treatment radiation so as to reduce excess radiation and peripheral organ damage. A planar array of radiation detectors is positioned below the patient during the treatment so that the patient lies directly on the array. The radiation treatment beam is set at a flux threshold that minimizes tissue damage (typically $1/10,000$ of the treatment flux) and at a level that permits the beam to just penetrate the patient. The treatment beam is turned on, and the detector outputs are monitored to determine the beam flux (i.e., particle current) that penetrates through the patient. The beam energy is modulated (i.e., adjusted in small discrete increments) to determine how the transmitted beam changes with beam energy. The accumulated incident flux data enables a curve of beam transmission vs. incident beam energy to be derived and enables treatment parameters to be accurately corrected at the time of treatment. Further, by comparing the experimentally derived attenuation with theoretically modeled attenuation, the modeling parameters may be corrected. Note that since the treatment correction is determined while the patient is in the treatment position, there is little or no organ motion between the treatment correction and irradiation. If the radiation array includes two-dimensional information, e.g. a planar array of radiation-sensitive detectors, then the beam alignment may be simultaneously checked with the patient in the final treatment position. This allows realignment of the treatment beam while the patient is in treatment position.

DETAILED DESCRIPTION OF THE INVENTION

Current radiation treatment of deep tumors involves many assumptions about how the patient's body absorbs radiation, and how to relate the diagnostic NMR or CAT images to radiation treatment parameters. Further, since internal organ motion and organ dimensions (e.g. intestinal contents) may change between the time of the diagnostic image acquisition and the irradiation treatment (these may be days apart), the planner must schedule an irradiation of much larger volumes than occupied by the tumor, increasing peripheral organ damage and the patient's radiation burden.

This invention comprises an in-situ procedure that allows treatment planning and eliminates corrections for organ motion and organ dimensions (since the procedure occurs with the patient in-place for treatment). Hence lower radiation doses and smaller radiation volumes can be achieved, reducing deleterious radiation side effects.

Figure 1:
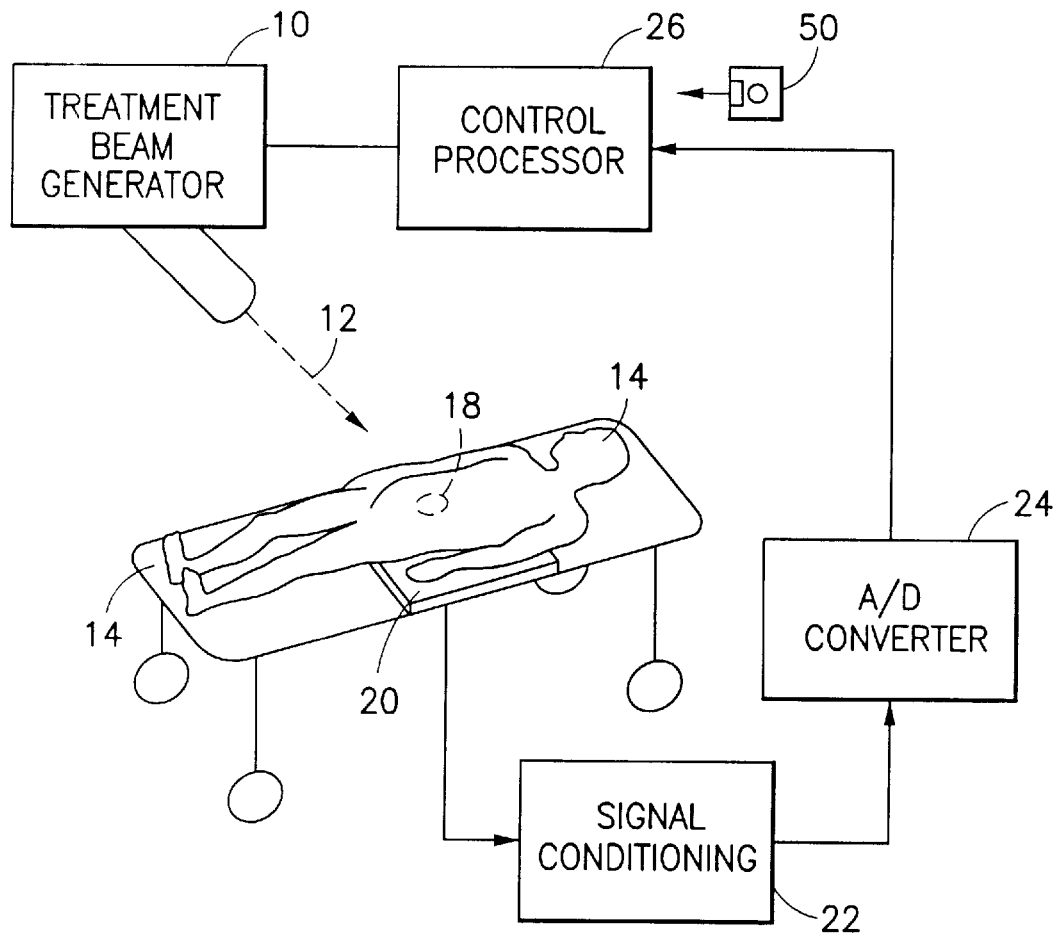
FIG. 1 is a high level schematic of the invention during a typical treatment.

A schematic of the layout of the invention is illustrated in FIG. 1 for a typical radiation treatment of an abdominal tumor. The radiation is emitted from a treatment beam generator 10 as a beam 12 of particles. The particles are typically x-rays, electrons, protons or pions. A patient 14 is placed on a gurney with the tumor 18 directly in line with treatment beam 12. A beam flux detector 20 is positioned directly beneath patient 14 so that tumor 18 is directly thereover. Outputs from flux detector 20 are fed via a signal conditioner 22 and an analog to digital converter 24 to a control processor 26 which provides overall control for the system.

Figure 2:
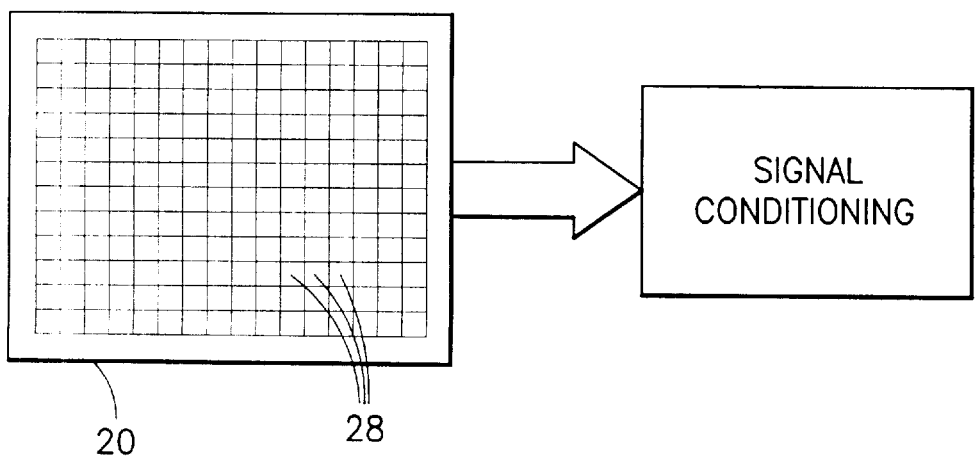
FIG. 2 is a top view of a two dimensional radiation flux detector that may be employed with the invention.

Referring to FIG. 2, a two dimensional flux detector 20 is illustrated and comprises an array of flux detector elements 28 that may be arranged in columns and rows, or any other desired configuration that will provide both incident flux position and current outputs indicative of the incident flux thereon. A plurality of flux detector element types are disclosed in copending U.S. patent application Ser. No. 09/241,503 filed Feb. 1, 1999, entitled "Focussing of Therapeutic Radiation On Internal Structures of Living Bodies" to the inventors hereof and assigned to the same Assignee. The disclosure of the aforesaid Application is incorporated herein by reference.

In brief, flux detector elements 28 may each comprise a semiconductor diode that is capable of producing electric signals of intensities that vary with the intensities of the incident flux thereon. In a further embodiment, each flux detector element 28 may comprise a scintillator material capable of producing light signals of intensities that vary with the intensities of the incident radiation. The light signals are detected via light transmitting fibers that are coupled to light detecting semiconductors. A still further embodiment may employ piezoelectric elements that produce electric signals of intensities that are proportional to incident flux. Accordingly, flux detector elements 28 may be embodied in a number of forms, so long as they provide signal outputs indicative of incident beam flux. Further, if beam position data is not required, a single broad flux detector may be used.

The Radiologist may vary treatment beam 12 so as to change a depth of penetration of the beam and the position of the treatment volume. The determination of the correct beam energy to use is based on calculations from medical scans, as described below. The proposed Radiologist's treatment plan derives a beam set-up that will place a desired beam flux within the treatment volume. A second plan is calculated using the same modeling parameters to predict a set-up that will allow the treatment beam to just penetrate through the patient.

The treatment beam is turned on, at about $1/10,000$ of the normal intensity, i.e., below the threshold level of significant radiation damage to tissue, at an energy to just penetrate the patient in accordance with the second plan described above. The beam energy is then modulated so that the beam cycles between barely transmitting through the body, and full transmission. The incident particle fluxes on flux detector 20 are measured and analyzed by control processor 26. This enables a determination to be made as to how the incident flux on flux detector 20 is altered by changes in original beam energy. From these measurements, a curve of incident flux on flux detector 20 versus original beam energy is derived. Recall, that these data are acquired at a treatment time when the patient is already in place.

Figure 3:
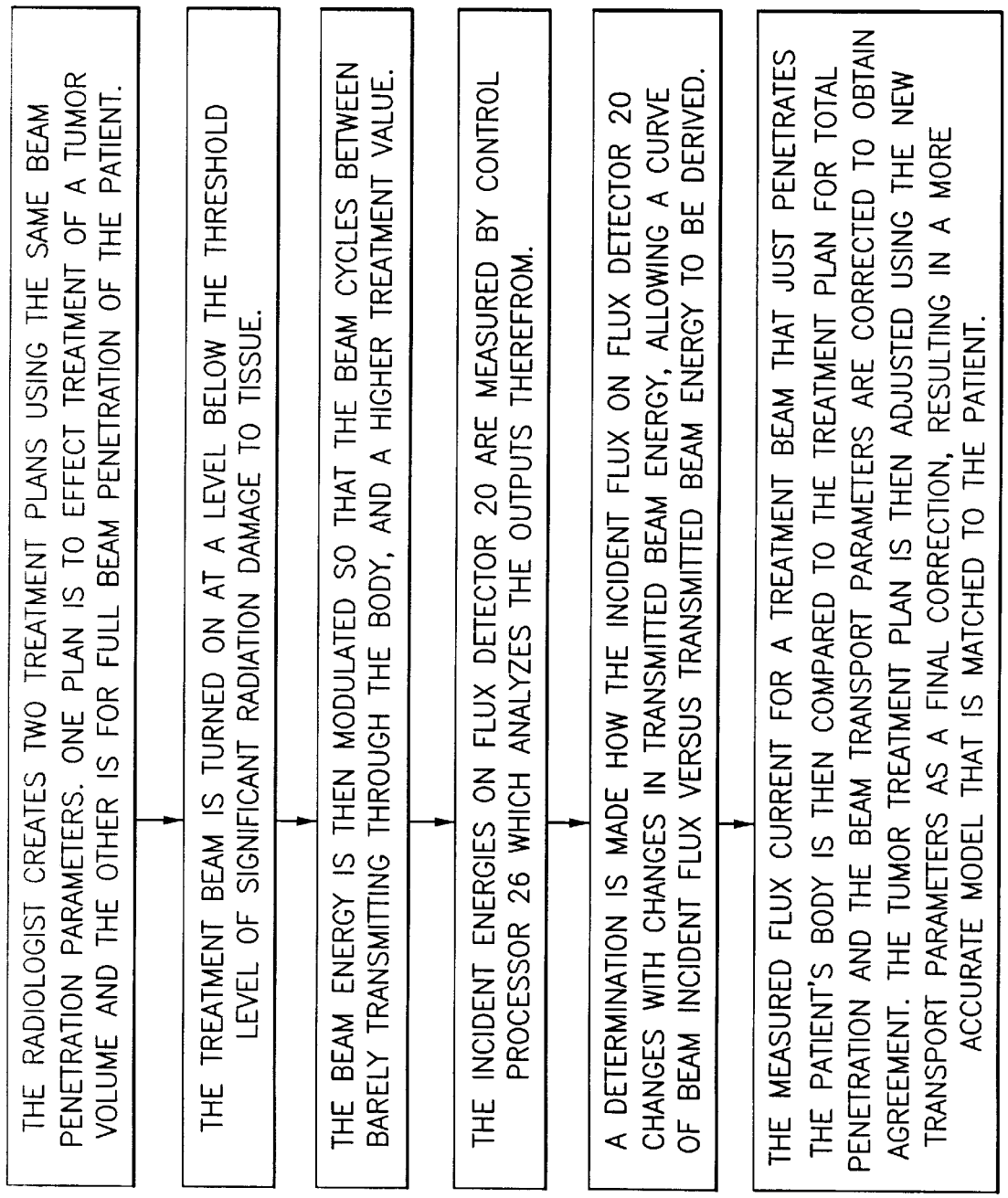
FIG. 3 is a high level logic diagram of the logic flow of the method of the invention.

The measured flux current for a treatment beam that just penetrates the patient's body is then used to correct the modeled treatment plan for total penetration of the patient, allowing the Radiologist to correct the modeling parameters and arrive at a more accurate model that is matched to the particular patient. In particular, the second model, based on the experimentally determined beam energy to achieve a flux that just penetrates through the patient's body, is used to correct the treatment beam energy derived as part of the first treatment plan. These steps are illustrated in the FIG. 3 and are further expanded upon in the remaining Figs.

Figure 4A:
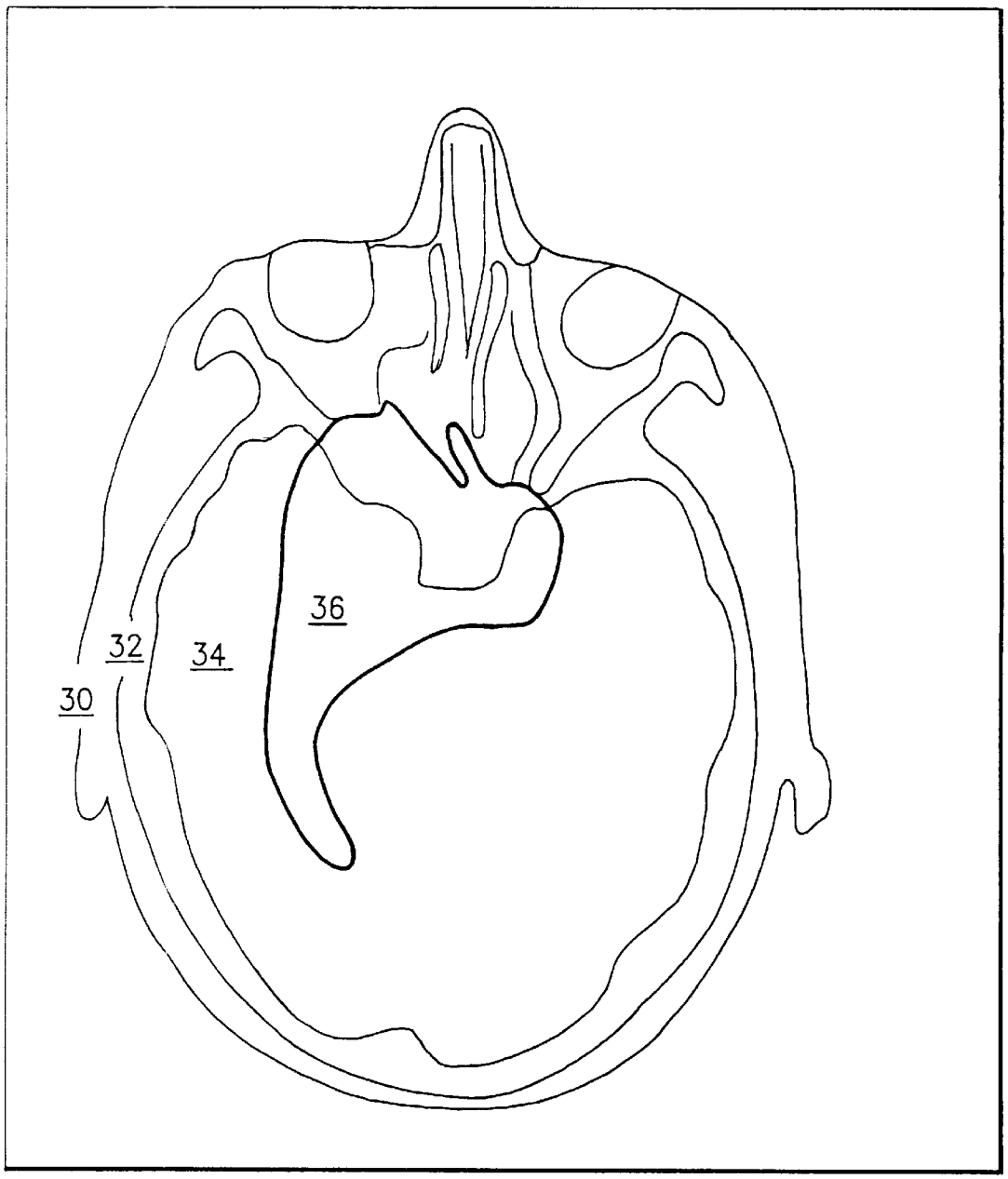
FIG. 4a is a schematic representing a CAT scan of a patient, with an embedded tumor.

FIG. 4a shows a cranial CAT scan with a region of a large tumor 36. The treatment of this tumor requires the radiation beam to penetrate the external skin tissue 30, skull bone 32, and brain tissue 34 before it reaches tumor 36. Since the image has been made using a CAT tool, the gray scale of the image corresponds to the relative absorption of x-rays by various types of tissue.

Figure 4B:
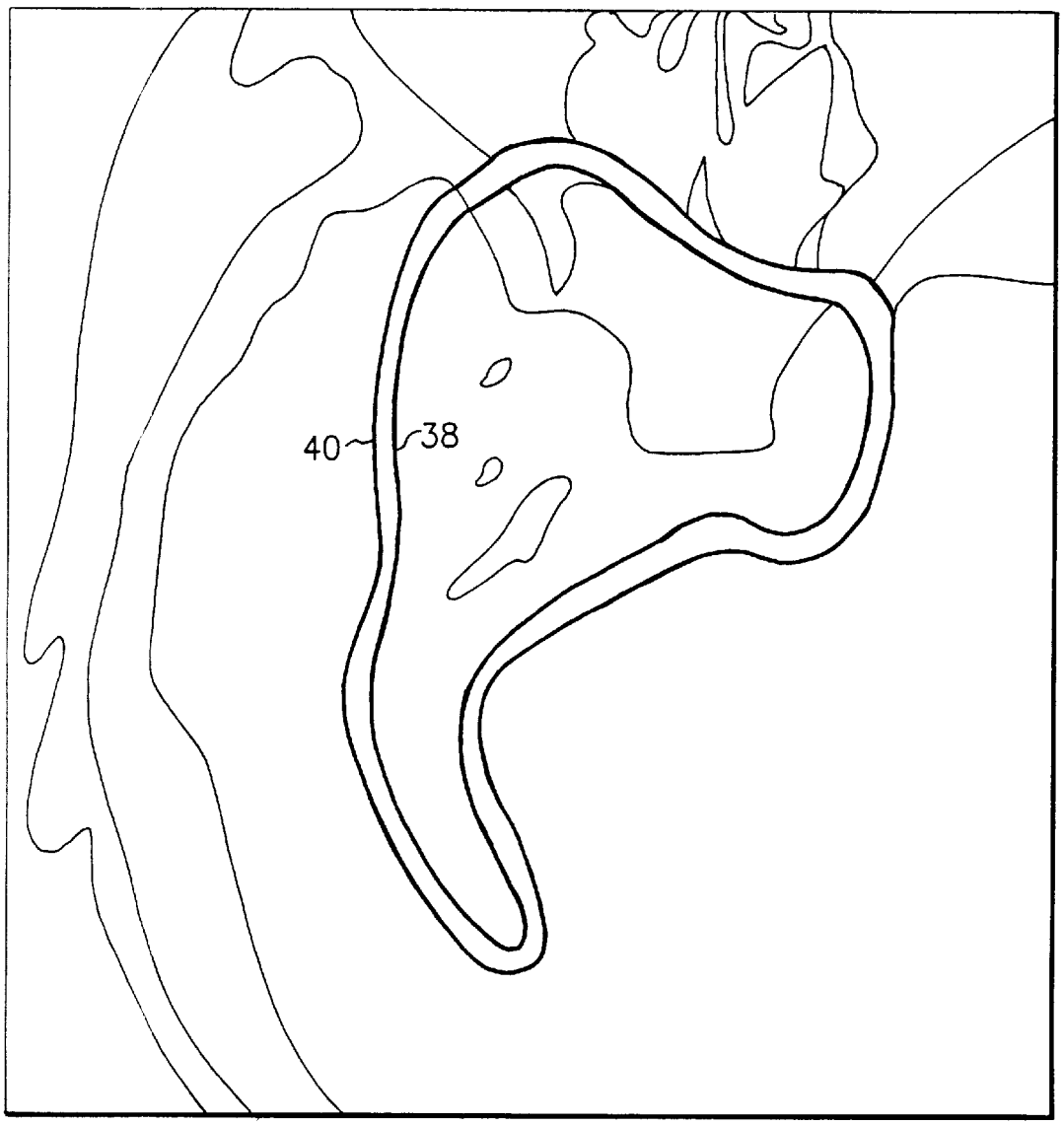
FIG. 4b is a schematic representing the CAT scan, tumor and treatment volume.

FIG. 4b shows a typical treatment plan by a Radiologist for tumor 36. The original tumor volume 38 has been enlarged by the Radiologist to a final irradiation treatment volume 40, an enlargement typically up to 30%, because of errors which may occur in the final treatment. Such errors may result from tumor motion from the position shown in the original scan (more common with abdominal tumors), and in errors in what may be called the Hounsfield Correction.

There are two stages in the identification and treatment of an internal tumor. Identification of the tumor may be done using a cross-sections scan, typically a CAT scan (computer aided tomography); a MRI scan (magnetic resonance imaging); or a PET scan (positron emission tomography). The treatment is done with a beam of different energy and perhaps of different particles. The Hounsfield Correction are tables which allow the Radiologist to scale the densities found in the original scan, to equivalent densities for energy loss and absorption of the treatment beam.

Figure 4C:
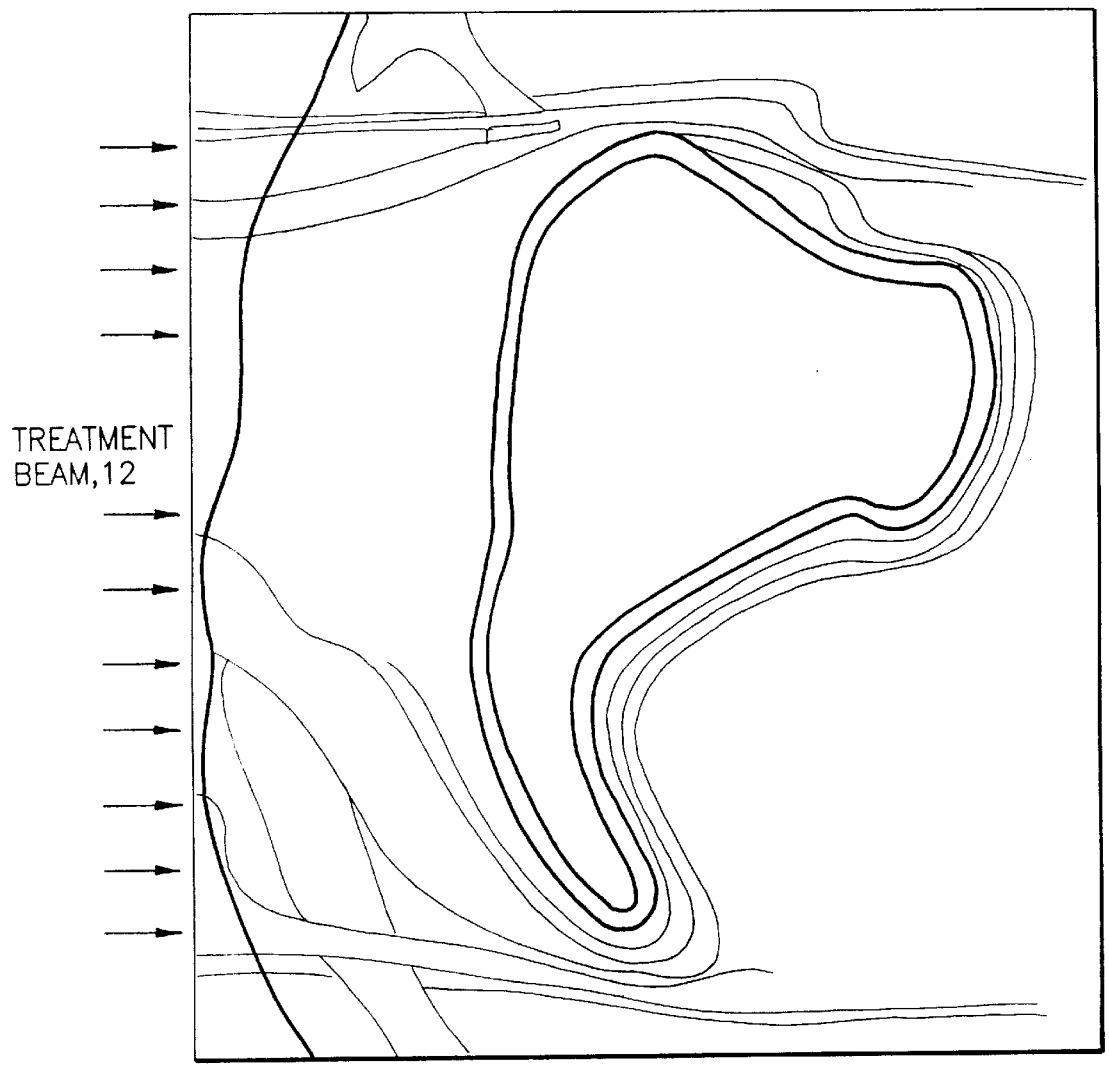
FIG. 4c is a schematic representing the CAT scan, tumor, treatment volume, and irradiation volume.
Figure 5:
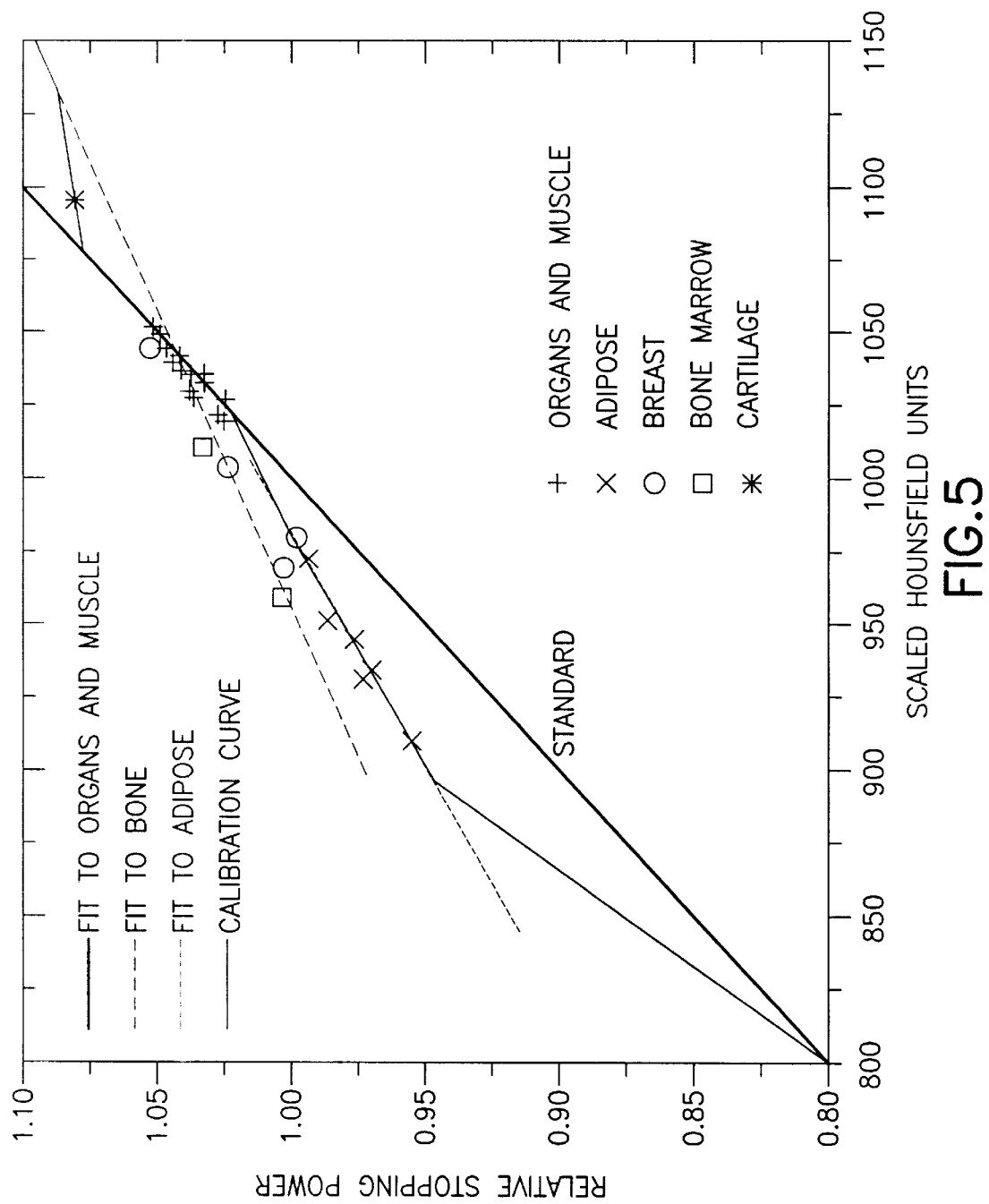
FIG. 5 is a schematic representing errors in the Hounsfield Correction used for treatment planning. The errors arise from CAT scan densities not scaling accurately to radiation treatment plans.

FIG. 4c shows a typical radiation treatment plan, based on the CAT scan of FIG. 4a. The Radiologist has used the variations in density of the CAT scan (indicated by shades of gray in the CAT image), to predict the energy loss and radiation deposition into the tumor site. Treatment beam 12 (entering from the left in FIG. 4c) may be protons, electrons or x-rays, at different energies from the exciting beam which was used to make the scan image. Because the deposition of energy into the patient has blurry edges, the irradiated volume is even bigger than the enlarged treatment volume indicated in FIG. 4b. Errors in the Hounsfield correction for this treatment plan are indicated in FIG. 5.

An extensive study of errors in the Hounsfield Correction for proton beams has been completed (see the Schaffner, Ph.D. Thesis cited above). This study evaluated the use of CAT scans for tumor identification, and an irradiation treatment plan using an energetic proton beam. FIG. 5, from this reference, shows the Hounsfield Correction for this situation as the solid line marked "Standard". The various data points, e.g. crosses, circles, squares, etc., show experimental values for a correction, based upon direct measurements. As indicated, for some kinds of tissue there are significant deviations between the "Standard" curve and the actual values. This is to be expected, since the absorption of x-rays in a CAT scan involves different physics from the energy loss of protons.

The error reported by Schaffner may be minimized by evaluating the accuracy of the treatment plan using the procedure of the invention. For deep tumors, the calculation of the required energy for the irradiation beam to just transit through the patient will include any errors included in the irradiation of the tumor volume. By comparing the experimentally determined transit energy to the treatment plan energy, a correction may be applied to the original treatment plan that will remove at least some of the errors shown in FIG. 5.

In addition to enabling revision of a treatment plan, the placement of flux detector 20 may be used to help in the positioning of treatment beam 12. More specifically, the direction of treatment beam 12 can be corrected by monitoring which of detector elements 28 output a highest level output. Then, since the position of flux detector 20 with respect to patient 14 is known, the alignment of treatment beam 12 can be corrected by determining a distance and direction to move the beam from a current position to a position that enables it to be incident on a desired detector element 28. The correction may also be made by moving the patient (and in some instances the sensor) relative to the treatment beam, leaving the beam fixed in position.

It should be understood that the foregoing description is only illustrative of the invention. Various alternatives and modifications can be devised by those skilled in the art without departing from the invention. For example, the invention has been described above based on the assumption that the controlling software/firmware that enables performance of the invention is already loaded into control processor 26. By contrast, it may be incorporated into a storage device 50 that may provide the necessary control code on an as needed basis. Accordingly, the present invention is intended to embrace all such alternatives, modifications and variances which fall within the scope of the appended claims.

What is claimed is:

1. A system for treating a volume of a patient through use of a radiation beam, said system comprising:
   a treatment beam source;
   a flux sensor positioned so that the patient is between the treatment beam source and the flux sensor, for outputting a signal indicative of an incident flux thereon from said treatment beam; and
   a processor for controlling said treatment beam source, said processor (i) controlling said treatment beam source to direct a treatment beam into said volume of said patient, (ii) monitoring said flux sensor to detect flux levels incident thereon, (iii) controlling said treatment beam source to change an emitted energy level of said treatment beam, and (iv) determining an effect of said change of emitted energy level upon said detected flux levels.

2. The system as recited in claim 1, wherein said processor controls said treatment beam source to modulate the emitted energy level of the treatment beam and determines an effect of said modulation upon signal outputs from said flux sensor.

3. The system as recited in claim 1, wherein said processor derives, from said effect upon said detected flux levels, a correction to a theoretically derived treatment beam energy level.

4. The system as recited in claim 1, wherein said flux sensor comprises a two dimensional array of flux sensors for provision of positional information regarding the treatment beam.

5. The system as recited in claim 4, wherein said processor employs signal outputs from said two dimensional array of flux sensors to adjust a beam direction relative to the patient.

6. The system as recited in claim 1, wherein said flux sensor comprises a plurality of semiconductor sensors whose outputs are dependent upon a level of incident treatment beam flux thereon.

7. The system as recited in claim 1, wherein said flux sensor comprises a plurality of scintillators whose light outputs are dependent upon a level of incident treatment beam flux thereon.

8. The system as recited in claim 1, wherein said processor:
   determines from said monitoring whether said treatment beam source requires adjustment to assure a desired level of treatment beam in said volume, and
   if required, adjusts said treatment beam source to achieve said desired level of treatment beam flux in said volume.

9. A method for treating a volume of a patient through use of a radiation beam system, said system including a treatment beam source, a flux sensor positioned so that the patient is between the treatment beam source and the flux sensor, said flux sensor outputting a signal indicative of an incident flux, and a processor, said method comprising the steps of:
   controlling said treatment beam source to direct a treatment beam at a volume of said patient;
   monitoring said flux sensor to detect flux levels of said treatment beam incident thereon;
   controlling said treatment beam source to change an emitted energy level of said treatment beam; and
   determining an effect of said change of emitted energy level upon said detected flux levels.

10. The method as recited in claim 9,
   wherein said step of controlling said treatment beam source to change an emitted energy level of said treatment beam comprises modulating the emitted energy level of the treatment beam; and
   wherein said step of determining an effect of said change of emitted energy level upon said detected flux levels comprises determining an effect of said modulation upon signal outputs from said flux sensor.

11. The method as recited in claim 9, further comprising deriving a correction for a theoretically derived treatment beam energy level.

12. The method as recited in claim 9, wherein said flux sensor comprises a two dimensional array of flux sensors, and wherein said method further comprises employing outputs sensed from said array of flux sensors to adjust a relative position of said patient and said treatment beam.

13. The method as recited in claim 12, wherein said relative position is adjusted by changing a direction of emission of said treatment beam from said treatment beam source.

14. The method of claim 9, further comprising:
   determining from said monitoring if said treatment beam source requires adjustment to assure a desired level of treatment beam flux in said volume; and if required, adjusting said treatment beam source to achieve said desired level of treatment beam flux in said volume.

15. A memory media including instructions for controlling a radiation system to treat a volume of a patient through use of a radiation beam system, said radiation beam system including a treatment beam source, a flux sensor positioned so that the patient is between the treatment beam source and the flux sensor, for outputting a signal indicative of an incident flux level thereon, and a processor, said memory media comprising:

means for operating said processor to control said treatment beam source to direct a treatment beam at a volume of said patient;

means for operating said processor to monitor said flux sensor to detect flux levels of said treatment beam incident thereon;

means for operating said processor to control said treatment beam source to change an emitted energy level of said treatment beam; and means for operating said processor to determine an effect of said change of emitted energy level upon said detected flux levels.

16. The memory media as recited in claim 15, further comprising means for operating said processor to modulate energy of said treatment beam to enable said processor to determine an effect of said modulation upon signal outputs from said flux sensor.

17. The memory media as recited in claim 16, further comprising means for operating said processor to derive a correction value to correct a theoretically derived treatment beam level.

18. The memory media as recited in claim 15, wherein said flux sensor comprises a two dimensional array of flux sensors, and wherein said memory media further comprises means for operating said processor to employ outputs sensed from said array of flux sensors to adjust a direction of emission of said treatment beam from said treatment beam source.

19. The memory media of claim 13, further comprising:

means for operating said processor to determine from said monitoring if said treatment beam source requires adjustment to assure a desired level of treatment beam flux in said volume, and means for operating said processor, if required, to adjust said treatment beam source to achieve said desired level of treatment beam flux in said volume.

\* \* \* \* \*